(12) United States Patent
Doron

(10) Patent No.: US 8,798,761 B2
(45) Date of Patent: Aug. 5, 2014

(54) SYSTEMS AND METHODS OF MONITORING THE ACOUSTIC COUPLING OF MEDICAL DEVICES

(75) Inventor: Eyal Doron, Kiriat-Yam (IL)

(73) Assignee: Cardiac Pacemakers, Inc., St. Paul, MN (US)

(*) Notice: Subject to any disclaimer, the term of this patent is extended or adjusted under 35 U.S.C. 154(b) by 270 days.

(21) Appl. No.: 12/427,312

(22) Filed: Apr. 21, 2009

(65) Prior Publication Data
US 2009/0326609 A1 Dec. 31, 2009

Related U.S. Application Data

(60) Provisional application No. 61/076,177, filed on Jun. 27, 2008.

(51) Int. Cl.
| | | |
|---|---|---|
| *A61N 1/00* | (2006.01) | |
| *A61B 5/00* | (2006.01) | |
| *A61N 1/372* | (2006.01) | |
| *A61B 8/00* | (2006.01) | |

(52) U.S. Cl.
CPC ........... *A61B 5/0031* (2013.01); *A61N 1/37217* (2013.01); *A61B 8/4281* (2013.01); *A61B 5/6843* (2013.01)
USPC .......................................................... 607/60

(58) Field of Classification Search
USPC .......................................................... 607/60
See application file for complete search history.

(56) References Cited

U.S. PATENT DOCUMENTS

| | | | |
|---|---|---|---|
| 2,463,533 A | * | 3/1949 | Harrison .................. 334/13 |
| 2,786,899 A | | 3/1957 | Carlisle et al. |
| 3,536,836 A | | 10/1970 | Pfeiffer |
| 3,672,352 A | | 6/1972 | Summers |
| 3,757,770 A | | 9/1973 | Brayshaw et al. |
| 3,805,796 A | | 4/1974 | Terry, Jr. et al. |
| 3,853,117 A | | 12/1974 | Murr |
| 3,943,915 A | | 3/1976 | Severson |

(Continued)

FOREIGN PATENT DOCUMENTS

| | | |
|---|---|---|
| EP | 0 499 939 | 8/1992 |
| EP | 0 928 598 | 12/1998 |

(Continued)

OTHER PUBLICATIONS

Harrison et al., "A Low-Power Low-Noise CMOS Amplifier for Neural Recording Applications," IEEE Journal of Solid-State Circuits 38(6):958-965, Jun. 2003.

(Continued)

*Primary Examiner* — Niketa Patel
*Assistant Examiner* — William Levicky
(74) *Attorney, Agent, or Firm* — Faegre Baker Daniels LLP

(57) ABSTRACT

Systems and methods for monitoring the acoustic coupling of medical devices is disclosed. An illustrative system for monitoring the acoustic coupling of an acoustic transducer attached to a patient's body includes a signal generator adapted to supply an electrical signal to the transducer, a circuit configured to measure at least one electrical parameter of the transducer, and a processor adapted to evaluate the degree of acoustic coupling of the transducer to the body based on the measured electrical signal. The processor can measure the frequency response of the acoustic transducer to the electrical signal, a time domain response of the acoustic transducer to the electrical signal, or a combination of both.

13 Claims, 8 Drawing Sheets

(56) References Cited

U.S. PATENT DOCUMENTS

| | | |
|---|---|---|
| 3,970,987 A | 7/1976 | Kolm |
| 4,026,276 A | 5/1977 | Chubbuck |
| 4,041,954 A | 8/1977 | Ohara |
| 4,062,354 A | 12/1977 | Taylor et al. |
| 4,082,097 A | 4/1978 | Mann et al. |
| 4,099,530 A | 7/1978 | Chen et al. |
| 4,127,110 A | 11/1978 | Bullara |
| 4,170,742 A | 10/1979 | Itagaki et al. |
| 4,206,761 A | 6/1980 | Cosman |
| 4,206,762 A | 6/1980 | Cosman |
| 4,265,252 A | 5/1981 | Chubbuck et al. |
| 4,281,666 A | 8/1981 | Cosman |
| 4,281,667 A | 8/1981 | Cosman |
| 4,340,038 A | 7/1982 | Mc Kean |
| 4,354,506 A | 10/1982 | Sakaguchi et al. |
| 4,361,153 A | 11/1982 | Slocum et al. |
| 4,378,809 A | 4/1983 | Cosman |
| 4,385,636 A | 5/1983 | Cosman |
| 4,407,296 A | 10/1983 | Anderson |
| 4,471,786 A | 9/1984 | Inagaki et al. |
| 4,481,950 A | 11/1984 | Duggan |
| 4,494,950 A | 1/1985 | Fischell |
| 4,519,401 A | 5/1985 | Ko et al. |
| 4,556,061 A | 12/1985 | Barreras et al. |
| 4,593,703 A | 6/1986 | Cosman |
| 4,596,255 A | 6/1986 | Snell et al. |
| 4,614,192 A | 9/1986 | Imran et al. |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,708,127 A | 11/1987 | Abdelghani |
| 4,719,919 A | 1/1988 | Marchosky et al. |
| 4,791,915 A * | 12/1988 | Barsotti et al. .................... 601/2 |
| 4,791,936 A | 12/1988 | Snell et al. |
| 4,793,825 A | 12/1988 | Benjamin et al. |
| 4,869,251 A | 9/1989 | Lekholm et al. |
| 4,885,002 A | 12/1989 | Watanabe et al. |
| 4,911,217 A | 3/1990 | Dunn et al. |
| 4,918,736 A | 4/1990 | Bordewijk |
| 5,074,310 A | 12/1991 | Mick |
| 5,113,859 A | 5/1992 | Funke |
| 5,117,835 A | 6/1992 | Mick |
| 5,160,870 A | 11/1992 | Carson et al. |
| 5,168,869 A | 12/1992 | Chirife |
| 5,184,605 A | 2/1993 | Grzeszykowski |
| 5,218,861 A | 6/1993 | Brown et al. |
| 5,279,292 A | 1/1994 | Baumann et al. |
| 5,291,899 A | 3/1994 | Watanabe et al. |
| 5,381,067 A | 1/1995 | Greenstein et al. |
| 5,423,334 A | 6/1995 | Jordan |
| 5,433,736 A | 7/1995 | Nilsson |
| 5,438,554 A * | 8/1995 | Seyed-Bolorforosh et al. ............................ 367/140 |
| 5,445,150 A | 8/1995 | Dumoulin et al. |
| 5,495,453 A | 2/1996 | Wociechowski et al. |
| 5,562,621 A | 10/1996 | Claude et al. |
| 5,619,997 A | 4/1997 | Kaplan |
| 5,620,475 A | 4/1997 | Magnusson |
| 5,704,352 A | 1/1998 | Tremblay et al. |
| 5,704,366 A | 1/1998 | Tacklind et al. |
| 5,712,917 A | 1/1998 | Offutt |
| 5,721,886 A | 2/1998 | Miller |
| 5,724,985 A | 3/1998 | Snell et al. |
| 5,743,267 A | 4/1998 | Nikolic et al. |
| 5,749,909 A | 5/1998 | Schroeppel et al. |
| 5,757,104 A | 5/1998 | Getman et al. |
| 5,759,199 A | 6/1998 | Snell et al. |
| 5,800,478 A | 9/1998 | Chen et al. |
| 5,807,258 A | 9/1998 | Cimochowski et al. |
| 5,814,089 A | 9/1998 | Stokes et al. |
| 5,833,603 A | 11/1998 | Kovacs et al. |
| 5,861,018 A | 1/1999 | Feierbach |
| 5,876,353 A | 3/1999 | Riff |
| 5,891,180 A | 4/1999 | Greeninger et al. |
| 5,904,708 A | 5/1999 | Goedeke |
| 5,925,001 A | 7/1999 | Hoyt et al. |
| 5,935,078 A | 8/1999 | Feierbach |
| 5,957,861 A | 9/1999 | Combs et al. |
| 5,967,989 A | 10/1999 | Cimochowski et al. |
| 6,015,387 A | 1/2000 | Schwartz et al. |
| 6,030,374 A | 2/2000 | McDaniel |
| 6,070,103 A | 5/2000 | Ogden |
| 6,140,740 A | 10/2000 | Porat et al. |
| 6,141,588 A | 10/2000 | Cox |
| 6,162,238 A | 12/2000 | Kaplan et al. |
| 6,164,284 A | 12/2000 | Schulman et al. |
| 6,167,303 A | 12/2000 | Thompson |
| 6,170,488 B1 | 1/2001 | Spillman, Jr. et al. |
| 6,176,840 B1 | 1/2001 | Nishimura et al. |
| 6,183,426 B1 | 2/2001 | Akisada et al. |
| 6,185,452 B1 | 2/2001 | Schulman et al. |
| 6,185,454 B1 | 2/2001 | Thompson |
| 6,185,460 B1 | 2/2001 | Thompson |
| 6,198,963 B1 | 3/2001 | Haim et al. |
| 6,198,965 B1 | 3/2001 | Penner et al. |
| 6,198,971 B1 | 3/2001 | Leysieffer |
| 6,200,265 B1 | 3/2001 | Walsh et al. |
| 6,236,889 B1 | 5/2001 | Soykan et al. |
| 6,237,398 B1 | 5/2001 | Porat et al. |
| 6,248,080 B1 | 6/2001 | Miesel et al. |
| 6,259,951 B1 | 7/2001 | Kuzma et al. |
| 6,260,152 B1 | 7/2001 | Cole et al. |
| 6,261,249 B1 | 7/2001 | Tallish et al. |
| 6,277,078 B1 | 8/2001 | Porat et al. |
| 6,315,721 B2 | 11/2001 | Schulman et al. |
| 6,427,088 B1 | 7/2002 | Bowman et al. |
| 6,431,175 B1 | 8/2002 | Penner et al. |
| 6,432,050 B1 | 8/2002 | Porat et al. |
| 6,442,413 B1 | 8/2002 | Silver |
| 6,442,433 B1 | 8/2002 | Linberg |
| 6,472,991 B1 | 10/2002 | Schulman et al. |
| 6,473,638 B2 | 10/2002 | Ferek-Petric |
| 6,564,807 B1 | 5/2003 | Schulman et al. |
| 6,577,899 B2 | 6/2003 | Lebel et al. |
| 6,584,352 B2 | 6/2003 | Combs et al. |
| 6,607,485 B2 | 8/2003 | Bardy |
| 6,628,989 B1 | 9/2003 | Penner et al. |
| 6,644,322 B2 | 11/2003 | Webb |
| 6,664,763 B2 | 12/2003 | Echarri et al. |
| 6,671,552 B2 | 12/2003 | Merritt et al. |
| 6,676,601 B1 | 1/2004 | Lacoste |
| 6,689,091 B2 | 2/2004 | Bui et al. |
| 6,712,772 B2 | 3/2004 | Cohen et al. |
| 6,731,976 B2 | 5/2004 | Penn et al. |
| 6,735,532 B2 | 5/2004 | Freed et al. |
| 6,754,538 B2 | 6/2004 | Linberg |
| 6,764,446 B2 | 7/2004 | Wolinsky et al. |
| 6,788,973 B2 | 9/2004 | Davis et al. |
| 6,790,187 B2 | 9/2004 | Thompson et al. |
| 6,799,280 B1 | 9/2004 | Edenfield et al. |
| 6,804,557 B1 | 10/2004 | Kroll |
| 6,826,430 B2 | 11/2004 | Faltys et al. |
| 6,855,115 B2 | 2/2005 | Fonseca et al. |
| 6,873,869 B2 | 3/2005 | Fischer |
| 6,960,801 B2 | 11/2005 | Lung |
| 6,970,037 B2 | 11/2005 | Sakhuja et al. |
| 6,978,181 B1 | 12/2005 | Snell |
| 6,985,088 B2 | 1/2006 | Goetz et al. |
| 6,985,773 B2 | 1/2006 | Von Arx et al. |
| 6,988,215 B2 | 1/2006 | Splett et al. |
| 6,993,393 B2 | 1/2006 | Von Arx et al. |
| 7,003,349 B1 | 2/2006 | Andersson et al. |
| 7,013,178 B2 | 3/2006 | Reinke et al. |
| 7,024,248 B2 * | 4/2006 | Penner et al. ................... 607/60 |
| 7,027,871 B2 | 4/2006 | Burnes et al. |
| 7,027,872 B2 | 4/2006 | Thompson |
| 7,035,684 B2 | 4/2006 | Lee |
| 7,060,030 B2 | 6/2006 | Von Arx et al. |
| 7,061,381 B2 | 6/2006 | Forcier et al. |
| 7,082,334 B2 | 7/2006 | Boute et al. |
| 7,096,068 B2 | 8/2006 | Mass et al. |

(56) References Cited

U.S. PATENT DOCUMENTS

| | | |
|---|---|---|
| 7,123,964 B2 | 10/2006 | Betzold et al. |
| 7,198,603 B2 | 4/2007 | Penner et al. |
| 7,203,551 B2 | 4/2007 | Houben et al. |
| 7,209,790 B2 | 4/2007 | Thompson et al. |
| 7,212,133 B2 | 5/2007 | Goetz et al. |
| 7,236,821 B2 | 6/2007 | Cates et al. |
| 7,273,457 B2 | 9/2007 | Penner et al. |
| 7,283,874 B2 * | 10/2007 | Penner .......................... 607/33 |
| 7,286,872 B2 | 10/2007 | Kramer et al. |
| 7,319,903 B2 | 1/2008 | Bange et al. |
| 7,335,161 B2 | 2/2008 | Von Arx et al. |
| 7,353,063 B2 | 4/2008 | Simms, Jr. |
| 7,469,161 B1 | 12/2008 | Gandhi et al. |
| 7,479,108 B2 | 1/2009 | Rini et al. |
| 7,617,001 B2 | 11/2009 | Penner et al. |
| 7,650,185 B2 | 1/2010 | Maile et al. |
| 7,756,587 B2 | 7/2010 | Penner et al. |
| 8,271,093 B2 | 9/2012 | Von Arx et al. |
| 8,340,776 B2 | 12/2012 | Doron et al. |
| 8,593,107 B2 | 11/2013 | Penner et al. |
| 2001/0025139 A1 | 9/2001 | Pearlman |
| 2002/0065540 A1 | 5/2002 | Lebel et al. |
| 2002/0077673 A1 | 6/2002 | Penner et al. |
| 2002/0151770 A1 | 10/2002 | Noll, III et al. |
| 2003/0114897 A1 | 6/2003 | Von Arx et al. |
| 2003/0212441 A1 | 11/2003 | Starkweather et al. |
| 2004/0039424 A1 | 2/2004 | Merritt et al. |
| 2004/0133092 A1 | 7/2004 | Kain |
| 2004/0152999 A1 | 8/2004 | Cohen et al. |
| 2004/0172083 A1 | 9/2004 | Penner |
| 2004/0210141 A1 | 10/2004 | Miller |
| 2005/0109338 A1 | 5/2005 | Stahmann et al. |
| 2005/0113705 A1 | 5/2005 | Fischell et al. |
| 2005/0136385 A1 | 6/2005 | Mann et al. |
| 2005/0159785 A1 | 7/2005 | Rueter |
| 2005/0159789 A1 | 7/2005 | Brockway et al. |
| 2005/0177135 A1 | 8/2005 | Hildebrand et al. |
| 2005/0203444 A1 * | 9/2005 | Schonenberger et al. ........ 601/2 |
| 2005/0265999 A1 | 12/2005 | Bush et al. |
| 2005/0288727 A1 | 12/2005 | Penner |
| 2006/0009818 A1 | 1/2006 | Von Arx et al. |
| 2006/0020307 A1 | 1/2006 | Davis et al. |
| 2006/0025834 A1 | 2/2006 | Von Arx et al. |
| 2006/0031378 A1 | 2/2006 | Vallapureddy et al. |
| 2006/0041287 A1 | 2/2006 | Dewing et al. |
| 2006/0041288 A1 | 2/2006 | Dewing et al. |
| 2006/0058627 A1 | 3/2006 | Flaherty et al. |
| 2006/0064134 A1 | 3/2006 | Mazar et al. |
| 2006/0064135 A1 | 3/2006 | Brockway |
| 2006/0064142 A1 | 3/2006 | Chavan et al. |
| 2006/0085039 A1 | 4/2006 | Hastings et al. |
| 2006/0094967 A1 | 5/2006 | Bennett et al. |
| 2006/0122667 A1 | 6/2006 | Chavan et al. |
| 2006/0142819 A1 | 6/2006 | Penner et al. |
| 2006/0149329 A1 | 7/2006 | Penner |
| 2007/0010742 A1 | 1/2007 | Torp et al. |
| 2007/0055313 A1 | 3/2007 | Stahmann et al. |
| 2007/0142728 A1 | 6/2007 | Penner et al. |
| 2007/0150014 A1 | 6/2007 | Kramer et al. |
| 2007/0162090 A1 | 7/2007 | Penner |
| 2007/0179549 A1 | 8/2007 | Russie |
| 2007/0250126 A1 | 10/2007 | Maile et al. |
| 2008/0015421 A1 | 1/2008 | Penner |
| 2008/0071178 A1 | 3/2008 | Greenland et al. |
| 2008/0103553 A1 | 5/2008 | Penner et al. |
| 2008/0108915 A1 | 5/2008 | Penner |
| 2008/0171941 A1 | 7/2008 | Huelskamp et al. |
| 2008/0195002 A1 | 8/2008 | Thompson et al. |
| 2008/0228094 A1 | 9/2008 | Audet et al. |
| 2008/0243007 A1 | 10/2008 | Liao et al. |
| 2008/0243210 A1 | 10/2008 | Doron et al. |
| 2009/0312650 A1 | 12/2009 | Maile et al. |
| 2010/0023091 A1 | 1/2010 | Stahmann et al. |
| 2011/0160804 A1 | 6/2011 | Penner |
| 2013/0218251 A1 | 8/2013 | Penner |
| 2013/0226259 A1 | 8/2013 | Penner |
| 2013/0238044 A1 | 9/2013 | Penner |

FOREIGN PATENT DOCUMENTS

| | | |
|---|---|---|
| EP | 1962557 | 8/2008 |
| JP | 10-505529 | 6/1998 |
| JP | 2002-515807 | 5/2002 |
| JP | 2004-041724 | 2/2004 |
| JP | 2004-511313 | 4/2004 |
| JP | 2004-537347 | 12/2004 |
| JP | 2005-521528 | 7/2005 |
| WO | WO88/02250 | 4/1988 |
| WO | WO96/26673 | 9/1996 |
| WO | WO98/43338 | 10/1998 |
| WO | WO 98/43701 | 10/1998 |
| WO | WO99/34453 | 7/1999 |
| WO | WO00/47109 | 8/2000 |
| WO | WO01/28627 | 4/2001 |
| WO | WO01/74278 | 10/2001 |
| WO | WO 01-76687 | 10/2001 |
| WO | WO01/97907 | 12/2001 |
| WO | WO02/03347 | 1/2002 |
| WO | 0232502 | 4/2002 |
| WO | WO 02/089904 | 11/2002 |
| WO | WO02/089904 | 11/2002 |
| WO | WO03/002243 | 1/2003 |
| WO | 03043688 | 5/2003 |
| WO | WO03/096889 | 11/2003 |
| WO | WO 2004-089465 | 10/2004 |
| WO | WO2005/009535 | 2/2005 |
| WO | WO2005/053786 | 6/2005 |
| WO | WO 2005-099816 | 10/2005 |
| WO | WO 2006-017615 | 2/2006 |
| WO | WO 2006-034183 | 3/2006 |
| WO | WO2006/060668 | 6/2006 |
| WO | WO 2006/126401 | 11/2006 |
| WO | WO2007/070794 | 6/2007 |
| WO | WO2007/080487 | 7/2007 |
| WO | WO2007/127696 | 11/2007 |
| WO | WO2008/118908 | 10/2008 |
| WO | WO 2010062538 A1 | 6/2010 |

OTHER PUBLICATIONS

IEEE Transactions on Biomedical Engineering, vol. 42, No. 5, May 1995, Title: Data Transmission from an Implantable Biotelemeter by Load-Shift Keying Using Circuit Configuration Modulator, by Zhengnian Tang, Brian Smith, John H. Schild, and P. Hunter Peckham, pp. 524-528.

Ishiwara et al., "Current Status and Prospects of FET-Type Ferroelectric Memories," Journal of Semiconductor Technology and Science 1(1): 1-14, Mar. 2001.

Neurosurgery Clinics of North America vol. 4, No. 4, Oct. 1993, Hydrocephalus, Title: The Treatment of Hydrocephalus by Paul M. Kanev, MD, and T.S. Park, MD., pp. 611-619.

Neurosurgery Clinics of North America, vol. 4, No. 4, Oct. 1993, Hydrocephalus, Title: Complications in Ventricular Cerebrospinal Fluid Shunting by Jeffrey P. Blount, MD, John A. Campbell, MD, and Stephen J. Haines, MD, pp. 633-656.

Neurosurgery Update II Vascular, Spinal, Pediatric, and Functional Neurosurgery, Published by McGraw-Hill, Inc., 1991, Editors Robert H. Wilkins, M.D., and Setti S. Rengachary, M.D., Title Shunt Complications by R. Michael Scott, pp. 300-319.

Neurosurgery, vol. 34, No. 5, May 1994, Concepts and Innovations, Title: A New Ventricular Catheter for the Prevention and Treatment of Proximal Obstruction in Cerebrospinal Fluid Shunts, by Enrique C.G. Ventureyra, M.D., F.R.C.S.(C)., F.A.C.S., Michael J. Higgins, M.D., pp. 924-926.

Neurosurgery, vol. 34, No. 6, Jun. 1994, Rapid Communication, Title: The Use of the Codman-Medos Programmable Hakim Valve in the Management of Patients with Hydrocephalus: Illustrative Cases, by Peter McL. Black, M.D., Ph.D., Rodolfo Hakim, M.D., Nancy Olsen Bailey, R.N., B.S.N., M.B.A., pp. 1110-1113.

(56) References Cited

OTHER PUBLICATIONS

Pediatric Neurosurgery 2nd Edition, Surgery of the Developing Nervous System, Published by W.B. Saunders Company Harcourt Brace Jovanovich, Inc., 1989. Title: Treatment of Hydrocephalus by Harold L. Rekate, M.D.; Ventricular Shunts: Complications and Results by Robert L. McLaurin, M.D.; pp. 200-229.

* cited by examiner

SYSTEMS AND METHODS OF MONITORING THE ACOUSTIC COUPLING OF MEDICAL DEVICES

CROSS-REFERENCE TO RELATED APPLICATION

This application claims priority under 35 U.S.C. §119 to U.S. Provisional Application No. 61/076,177, filed on Jun. 27, 2008, entitled "Systems and Methods Of Monitoring The Acoustic Coupling of Medical Devices," which is incorporated herein by reference in its entirety for all purposes.

TECHNICAL FIELD

The present invention relates generally to medical devices employing acoustic transducers for transcutaneously transmitting and receiving acoustic signals from within the body. More specifically, the present invention pertains to systems and methods for monitoring the acoustical coupling of medical devices.

BACKGROUND

Acoustic transducers are utilized in a variety of medical applications for transmitting and receiving acoustic signals through the body. In cardiac rhythm management applications, for example, acoustic transducers can be used for telemetrically communicating with and powering implantable medical devices, and for providing therapy to a patient. An example telemetry system employing acoustic transducers is described, for example, in U.S. Pat. No. 7,024,248 to Penner et al., entitled "Systems and Methods For Communicating With Implantable Devices," which is incorporated herein by reference in its entirety for all purposes. Acoustic transducers are frequently utilized in other medical fields such as medical imaging (e.g., ultrasonography) to permit non-invasive visualization of internal body structures or organs within the body.

In some cases, piezoelectric transducers are used to generate acoustic waves that can be transcutaneously transmitted into or received from the body. Such devices are typically placed in intimate contact with the patient's skin, and utilize the mechanical and electrical properties of piezoelectric materials to enable electrical to acoustic transduction. To facilitate the transmission and receipt of acoustic waves through the skin, an acoustic coupling medium (e.g., an acoustic gel) is sometimes used to reduce or eliminate the presence of air at the interface between the skin and the transducer, which due to its low acoustical impedance, can cause reflection and attenuation losses of the acoustic energy at the interface.

As a result of this property of acoustic interfaces, individuals wearing acoustic devices must often confirm the proper placement of the acoustic transducer on the skin, and in some cases must ensure that an adequate coupling medium is present on the surface of the skin to provide adequate impedance coupling at the transducer/skin interface. For untrained individuals unfamiliar with such devices, or in those cases where the device is to be placed on the skin for extended periods of time, the monitoring of the acoustic coupling may be difficult or even prohibitive. In certain settings such as in an ambulatory setting, for example, the acoustic transducer may become dislodged from the skin, requiring the individual or caregiver to reapply the transducer to reestablish the acoustic transmission.

SUMMARY

The present invention pertains to systems and methods for monitoring the acoustical coupling of medical devices. An illustrative system for monitoring the coupling of an acoustic transducer attached to a patient's body includes an acoustic transducer in communication with an implantable medical device, a signal generator adapted to supply an electrical signal to the acoustic transducer, a circuit configured to measure at least one electrical parameter of the acoustic transducer, and an evaluation module adapted to evaluate the degree of acoustic coupling of the transducer to the body based on the measured electrical parameter. In some embodiments, the evaluation module is configured to evaluate the degree of acoustic coupling by sensing a frequency parameter associated with the acoustic transducer. In other embodiments, the evaluation module is configured to evaluate the degree of acoustic coupling based on a time domain parameter associated with the acoustic transducer. In further embodiments, both a frequency parameter and a time domain parameter may be used to evaluate the degree of acoustic coupling.

A method of monitoring the coupling of an acoustic transducer attached to patient's body can include providing an electrical signal to the acoustic transducer, measuring at least one electrical parameter associated with the response of the acoustic transducer to the electrical signal, and evaluating the degree of acoustic coupling of the acoustic transducer to the body based on the measured electrical parameter. In some embodiments, the electrical parameter sensed may comprise a voltage and/or current parameter associated with the acoustic transducer. In one embodiment, the electrical signal provided to the acoustic transducer is swept across a range of different frequencies, and the step of evaluating the degree of acoustic coupling of the transducer to the body includes measuring an impedance parameter at multiple frequencies. In other embodiments, evaluating the acoustic coupling includes measuring a time domain parameter associated with the response of the acoustic transducer to the electrical signal. In further embodiments, evaluating the acoustic coupling includes measuring the complex impedance of an equivalence electrical circuit modeling the acoustic transducer.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
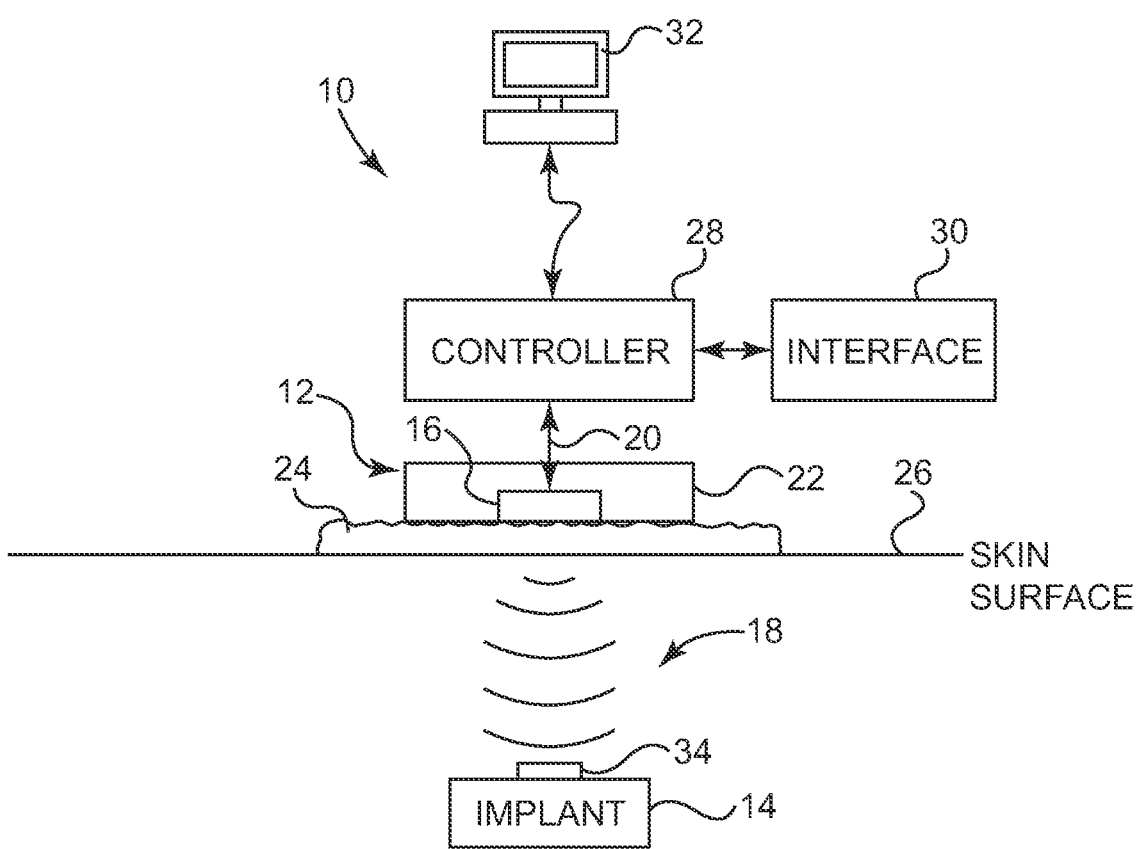
FIG. 1 is a schematic view showing an illustrative system for transcutaneously communicating with an implantable medical device.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view showing an illustrative system 10 for transcutaneously communicating with an implantable medical device. As shown in FIG. 1, the system 10 includes an external device 12 in acoustic communication with an implantable medical device 14 located within a patient's body. In certain embodiments, for example, the external device 12 comprises an external monitor adapted to transmit and receive acoustic signals to and from an implanted pressure sensor 14 that senses pressure at a location within the body. An example pressure sensor adapted to sense arterial blood pressure is disclosed, for example, in U.S. Pat. No. 6,277,078, entitled "System and Method for Monitoring A Parameter Associated With The Performance Of A Heart," which is incorporated herein by reference in its entirety for all purposes.

The implantable medical device 14 can be configured to sense other physiological parameters within the body. Examples of other physiological parameters that can be sensed by the implantable medical device 14 include, but are not limited to, blood flow, temperature, and strain. Various electrical, chemical, and/or magnetic properties may also be sensed within the body via the implantable medical device 14. Although only one implantable medical device 14 is shown in the illustrative system 10 of FIG. 1, multiple implantable medical devices 14 can be in acoustic communication with the external device 12 and/or with other devices located outside or inside the patient's body.

The external device 12 includes an acoustic transducer 16 adapted to communicate with the implanted medical device 14 by transmitting an acoustic wave 18 transcutaneously into the body. In certain embodiments, the acoustic transducer 16 is configured to operate as both a transmitter and receiver. In a transmission mode of operation, the acoustic transducer 16 is energized via an electrical signal 20, which is converted by the transducer 16 into acoustic energy for generating an acoustic wave 18 that can be received by the implantable medical device 14. In a receiver mode of operation, the acoustic transducer 16 is configured to convert acoustic waves 18 transmitted by the implantable medical device 14 into electrical energy. In an alternative embodiment, separate acoustic transducers can be provided for transmitting and receiving acoustic waves 18 within the body. In one such embodiment, for example, a first acoustic transducer is used for transmitting acoustic waves into the body whereas a second acoustic transducer is used for receiving acoustic waves from within the body.

The acoustic transducer 16 can be held against the patient's body, or alternatively, can be coupled to the patient's body via a patch, strap, belt, or other suitable attachment means 22. An acoustic coupling material 24 may be applied between the patient's skin 26 and the acoustic transducer 16 to facilitate the transmission of acoustic energy through the skin 26. Examples of suitable acoustic coupling materials 24 can include hydrogel, silicone, polyurethane, or the like. An illustrative patch that can be used to couple the acoustic transducer 16 to the patient's skin 26 is described, for example, in U.S. Pat. No. 7,024,248, entitled "Systems and Methods For Communicating With Implantable Devices," which is incorporated herein by reference in its entirety for all purposes.

The external device 12 is coupled to a controller 28 that controls the operation of the external device 12, including the delivery of electrical signals 20 to the acoustic transducer 16 for monitoring the transducer 16. An interface 30 such as a graphical user interface (GUI) may be used to monitor the status of the external device 12, including the frequency and amplitude of the electrical signal 20 provided to the acoustic transducer 16 as well as the degree of acoustic coupling between the transducer 16 and the body. The interface 30 can also be used to monitor other aspects of the external device 12, including the monitoring of sensor and status data transmitted from the implantable medical device 14. Although the controller 28 and interface 30 are shown as separate components in FIG. 1, in other embodiments the controller 28 and/or monitor 30 may be provided as a component of the external device 12, or as a component of another device located outside or inside the body.

The controller 28 can be linked to an external system 32 used to monitor the data received from the external device 12, the implantable medical device 14, as well as other communicating devices. In some embodiments, for example, the external system 32 comprises a remote patient management system such as the LATITUDE® system available from Boston Scientific of Natick, Massachusetts.

During operation, the controller 28 can be used to control, energize, and/or otherwise communicate with the implantable medical device 14. In some embodiments, for example, the controller 28 can be tasked to activate the implantable medical device 14 by transmitting one or more acoustic waves 18 into the body that are received by an acoustic transducer 34 coupled to implantable medical device 14. Upon excitation from the acoustic waves 18, the implantable medical device 14 may wake-up from an initial, sleep state and transition to an active, powered state and take one or more measurements within the body and/or perform some other designated task within the body. The data sensed by the implantable medical device 14 can then be transmitted to the external device 12 for further analysis.

In some embodiments, the acoustic transducer 16 comprises a piezoelectric transducer having a number of terminal leads electrically connected to the controller 28. Piezoelectric materials are characterized in their ability to generate an electrical potential in response to an applied mechanical stress. Example piezoelectric materials suitable for use in piezoelectric transducers are piezo-ceramics such as lead zirconate titanate (PZT). As discussed further herein, the mechanical to electrical coupling provided by these materials enables the sensing of the mechanical environment at the transducer/body interface by sensing various parameters associated with the electrical signal 20 generated by the controller 28.

The acoustic transducer 16 can be modeled as a linear, four terminal device with one portion of the device existing in the electrical realm and another portion existing in the mechanical-acoustic realm. The piezoelectric properties of the transducer material link the electrical and mechanical-acoustic portions of the device together via a linear relationship. The mechanical-acoustic portion of this relationship can be modeled using an electrical analogy where the force of the acoustic waves exerted on the transducer face represents a voltage whereas a volumetric movement of the face represents a current. The acoustic transducer 16 can thus be modeled as an electrical circuit having a number of resistors, capacitors, and inductors.

Figure 2:
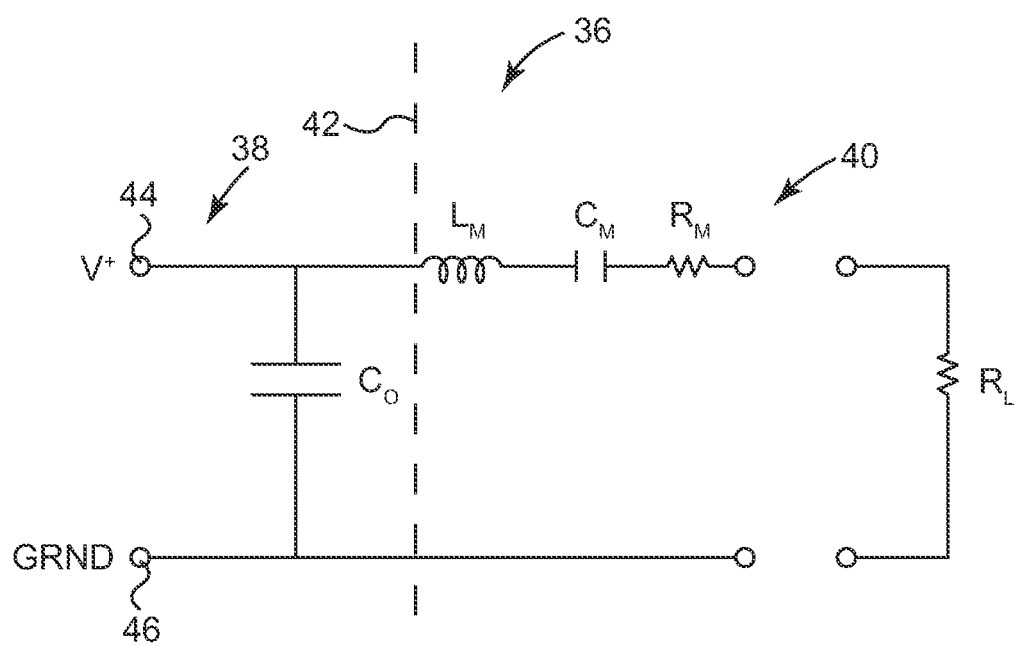
FIG. 2 is a block diagram showing an equivalence circuit for the acoustic transducer of FIG. 1.

FIG. 2 is a block diagram showing an equivalent electrical circuit 36 for the acoustic transducer 16 of FIG. 1. As shown in FIG. 2, the electrical circuit 36 comprises an electrical portion 38 and a mechanical-acoustic portion 40 separated from each other via a dividing line 42, which represents the electromechanical link provided by the piezoelectric material. The electrical portion 38 denotes the electrical dynamics of the circuit 36, and includes a set of terminals 44,46 which represent the terminal leads of the acoustic transducer 16. The clamped electrical capacitance of the acoustic transducer 16, in turn, is represented in the circuit 36 as a capacitor $C_0$, which for some piezoelectric transducers is formed by electrodes deposited on each side of a piezoelectric material. The capacitance $C_0$ of the acoustic transducer 16 is typically large based on the high dielectric coefficient of the piezoelectric material.

The mechanical-acoustic portion 40 of the circuit 36 represents the mechanical dynamics of the system. An inductor $L_M$ represents the effective mass of the acoustic transducer 16, where the mechanical inertia of the transducer 16 opposes acceleration in the same way as inductance opposes a change of current. A capacitor $C_M$ represents the elastic force of the acoustic transducer 16, where an applied voltage stores charge in the same way as an applied force effectively stores displacement. A resistor $R_M$, in turn, represents the frictional losses associated with the acoustic transducer 16. The link 42 between the electrical portion 38 and the mechanical-acoustic portion 40 of the circuit 36 is established by the piezoelectric effect of the acoustic transducer 16.

The mechanical-acoustic portion 40 of the circuit 36 is closed by a load impedance $R_L$, which represents the impedance of the medium coupling the acoustic transducer 16 to the patient's body. For an acoustic transducer operating in air, for example, the load impedance $R_L$ is very low, and is thus essentially a short circuit. This is due to the relative softness of air relative to water since only a small amount of force (voltage) is required to induce a velocity (current) in the air molecules surrounding the transducer surface. When the acoustic transducer 16 is acoustically coupled to the patient's body, however, less acoustic energy is reflected at the transducer/body interface, resulting in a greater amount of energy entering into the patient's body. This results in an increase in the load resistance $R_L$ from the zero load state occurring when the acoustic transducer 16 is operating in air.

While the load impedance $R_L$ is modeled as a pure resistance in the circuit 36 of FIG. 2, the impedance $R_L$ will normally have an inductive component as well since the vibrations on the transducer surface normally carry an additional mass of water that moves back and forth with the surface, thus adding to the inertial mass of the transducer. This additional mass may be negligible relative to the mass represented by $L_M$, or can be considerable depending on the design of the transducer.

The electrical circuit 36 depicted in FIG. 2 exhibits a resonance. When the load resistance $R_L$ is low (e.g., when the acoustic transducer is operating in air and exhibits little loss), the acoustic transducer 16 exhibits a series resonance (i.e., a maximum of the conductance) at a frequency of approximately $f_R \approx 1/\sqrt{2\pi L_M C_M}$. At this frequency $f_R$, the motional inductance and capacitance cancel each other such that the resonance is a purely mechanical resonance. The value of the real part of the conductance at resonance is $1/R_M$. The width of the real part of the conductance is approximately $\Delta f \approx f_R \sqrt{2\pi f_R R_M C_M}$. Because of the existence of the electrical capacitance $C_0$, there is also a second resonant condition at $$f_A = f_R \sqrt{\frac{C_0 + C_M}{C_0}}.$$

This resonance is a parallel resonance (i.e., a maximum of the resistance), and is a combined mechanical and electrical effect.

The behavior of the impedance curves for the electrical circuit 36 changes based on the degree of acoustic coupling provided between the acoustic transducer 16 and the transducer/body interface. Any dissipative portion of the radiation load of the acoustic transducer 16 adds to $R_M$ while any inductive portion adds to $L_M$. Thus, in the presence of sufficient acoustic coupling, the resonance of the circuit 36 will tend to decrease in height and increase in width. The resonance frequency $f_R$ will also tend to decrease in the presence of sufficient acoustic coupling.

While FIG. 2 depicts an illustrative circuit 36 modeling the acoustic transducer 16 of FIG. 1, it should be understood that other circuits may be used to model the transducer and coupling behavior. A more complex equivalence circuit could involve, for example, multiple resonances in close proximity as well as changes in circuit element values (e.g., $L_M$) depending on frequency. Another equivalence circuit can include a matching circuit between the terminal leads and a measuring device. The matching circuit may comprise, for example, any combination of inductors, capacitors, transformers, and resistors, whether in parallel, series, or a combination of both. In use, the matching circuit can be used to match the resulting electrical impedance to that of the driving circuit so as to enhance the efficiency and/or sensitivity of the system. While the presence of a matching circuit may complicate the behavior of the impedance, the impedance is still sensitive to the presence of acoustic coupling, and therefore can be used to monitor the electrical impedance of the acoustic transducer 16.

The impedance characteristics of the acoustic transducer 16 can be further understood in terms of its time-domain characteristics. The impedance characteristics of the acoustic transducer 16 can be expressed in the Laplace domain in the following form:

$$Z(s) = \frac{V(s)}{I(s)}, I(s) = V(s)Z^{-1}(s), V(s) = I(s)Z(s).$$

In the time-domain, this can be expressed as:

$$I(s)=V(t) \otimes Y(t), V(t)=I(t) \otimes Z(t)$$

where $Z(t)$ is the inverse Laplace transform of $Z(s)$, and $Y(t)$ is the inverse Laplace transform of $Z^{-1}(s)$. The $\otimes$ symbol in the above expression denotes a convolution. For the illustrative equivalence circuit 36 depicted in FIG. 2, for example, the Laplace space impedance of the acoustic transducer 16 can be written in the following form:

$$Z(s) = s^{-1} \frac{s^2 + \omega_0^2 \tau s + \omega_0^2}{C_0 s^2 + \tau \omega_0^2 C_0 s + \omega_0^2 (C + C_0)},$$

$$\tau = (R_M + R_L) C_M, \quad \omega_0^2 = \frac{1}{(L_M + L_L) C_M}$$

To obtain I(t), for example, Y(t) must thus be evaluated. Since Z(s) is a rational function of s, the inverse Laplace transform of its reciprocal has the form of a sum of decaying exponentials. There is one decaying exponential for every root of the numerator of Z(s), with the s value corresponding to the root placed in the exponent. This can be expressed generally as:

$$Y(t) = \sum_n A_n \exp(s_n t)$$

For the illustrative equivalence circuit 36 of FIG. 2, for example, there would be two roots at:

$$s_{1,2} = -\frac{\omega_0^2 \tau}{2} \pm i\omega_0 \sqrt{1 - \frac{\omega_0^2 \tau^2}{2}}$$

Each root donates one exponential, which oscillates at a frequency which is close to $\omega_0/2\pi$, and decays with the following time constant:

$$\frac{\omega_0^2 \tau}{2} = \frac{R_M + R_L}{2(L_M + L_L)}$$

The roots always appear as either real roots or conjugate pairs, since the resulting time-domain kernel Z(t) or Y(t) are always real.

Figure 3:
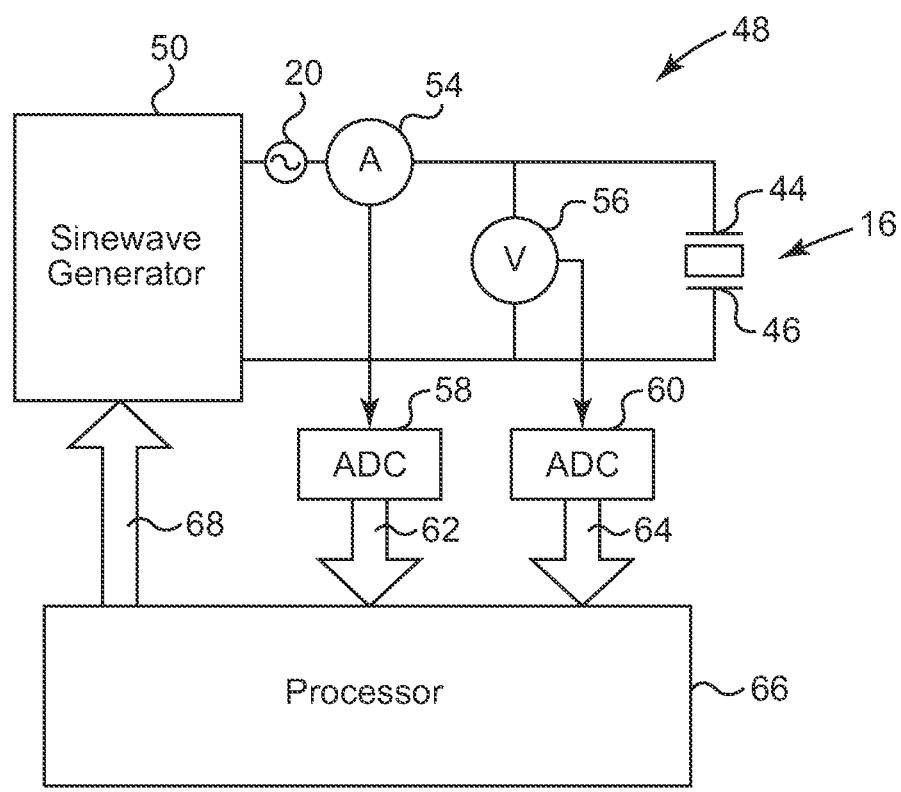
FIG. 3 is a block diagram showing an illustrative system for monitoring the acoustic coupling of an acoustic transducer attached to a patient's body.

FIG. 3 is a block diagram showing an illustrative system 48 for monitoring the acoustic coupling of an acoustic transducer 16 attached to a patient's body. As shown in FIG. 3, the system 48 includes a signal generator 50 adapted to generate a time-varying electrical signal 20 that can be applied across the terminal leads 44,46 of the acoustic transducer 16. In certain embodiments, for example, the signal generator 50 provides a sinusoidal electrical signal 20 across the terminal leads 44,46 at a desired frequency, or across a range of frequencies. The signal 20 generated by the signal processor 50 is passed through an ammeter 54, which measures the current across the terminal leads 44,46. The signal 20 is further fed to a voltmeter 56, which measures the voltage differential across the terminal leads 44,46. In some embodiments, the ammeter 54 and voltmeter 56 are configured to measure both the amplitude and the phase of the measured signal.

The measured current and voltage signals are fed to respective analog-to-digital (A/D) converters 58,60, which convert the measured analog signals into corresponding digital signals 62,64. The digitized signals 62,64 are then fed to an evaluation module 66 such as a processor or an analog or digital decision circuit that analyzes the frequency of the electrical signal 20 generated by the signal generator 50 and the current and voltage signals 62,64 outputted by the A/D converters 58,60. Using the frequency, current, and voltage inputs, the evaluation module 66 then evaluates the complex impedance of the acoustic transducer 16 according to the following equation:

$$Z(f) = \frac{\langle V(t) \exp(-2\pi i f t) \rangle_T}{\langle I(t) \exp(-2\pi i f t) \rangle_T}$$

In the above equation, the angular brackets denote an average over a time period sufficiently large to provide the desired frequency resolution. A similar result can be obtained using other representations in lieu of the above equation, however. In one alternative, for example, the absolute value and phase of the impedance can be expressed as follows:

$$|Z|^2 = \frac{\langle V(t)^2 \rangle_T}{\langle I(t)^2 \rangle_T}, \quad \cos\phi = \frac{\langle V(t) I(t) \rangle_T}{\sqrt{\langle V(t)^2 \rangle_T \langle I(t)^2 \rangle_T}}$$

which may be computationally easier and faster to perform in a microprocessor since it uses only real arithmetic.

In the embodiment of FIG. 3, the evaluation module 66 is configured to evaluate the degree of acoustic coupling by sweeping the electrical signal 20 across a frequency range, and at each frequency or at certain frequencies, measuring the complex impedance associated with the acoustic transducer 16. The sweeping of the frequency can be accomplished, for example, via a control signal 68 from the evaluation module 66 that adjusts the frequency of the electrical signal 20 generated by the signal generator 50, either across a continuum of frequencies or at multiple, discrete frequencies. The frequency span will typically be in the vicinity of the resonance frequency of the acoustic transducer 16, and as such, will typically vary based on the resonance characteristics of the transducer 16.

In another embodiment, the electrical signal 20 comprises a wideband signal simultaneously containing a range of frequencies. For example, the electrical signal 20 may comprise noise produced using a random number generator, which may also be filtered to the desired frequency range using a software or hardware filter. In such embodiment, the evaluation module 66 constructs the frequency-dependent complex impedance curve by passing the received voltage and current signals through a filter bank, such as a Fourier Transform or fast Fourier Transform (FFT), and processes each frequency component independently to construct the impedance curve. An average over several of these random excitations may also be performed in order to improve the accuracy.

Figure 4:
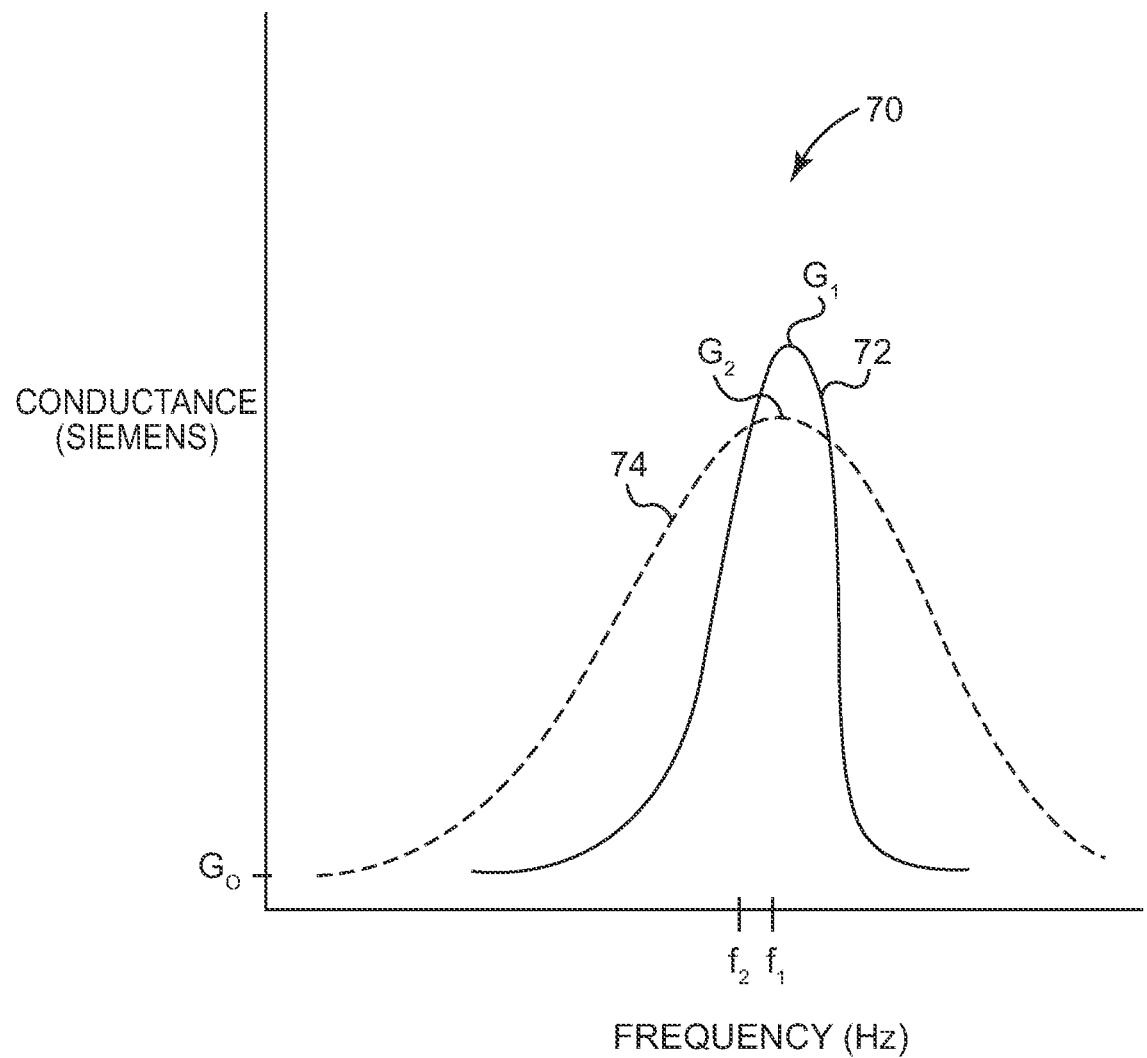
FIG. 4 is a graph showing the conductance versus frequency for two acoustic coupling scenarios.

The evaluation module 66 is configured to analyze the resultant impedance curve to determine whether a sufficient degree of acoustic coupling is present at the transducer/body interface. In certain embodiments, for example, the evaluation module 66 determines the frequency at which maximal conductance occurs, and the width of the conductance peak. This can be further understood with respect to the graph 70 in FIG. 4, which shows the frequency (in Hz) versus conductance (in Siemens) for two acoustic coupling scenarios. The solid conductance curve 72 in the graph 70 may represent, for example, the conductance of the acoustic transducer 16 as a function of frequency when poor acoustic coupling exists. The dashed conductance curve 74, in turn, may represent the conductance of the acoustic transducer 16 when sufficient acoustic coupling exists.

As can be seen by a comparison of the two conductance curves 72,74, the maximal conductance $G_1$ during poor acoustic coupling tends to be greater than the maximum conductance $G_2$ when sufficient acoustic coupling is present. The width of the conductance curve 74 when sufficient coupling is present also tends to be greater than the width of the conductance curve 72 during poor acoustic coupling. A decrease in frequency from $f_1$ to $f_2$ also occurs when sufficient acoustic coupling is present.

The evaluation module 66 can be configured to analyze the frequency $f_1,f_2$ of maximum conductance $G_1,G_2$ and the width of the conductance curves 72,74 in order to determine whether the acoustic coupling is within a desired range. For conductance curve 72, for example, the evaluation module 60 may analyze the frequency $f_1$ associated with the peak conductance $G_1$ along with the width of the curve 72 from a nominal conductance value $G_0$ to the peak conductance $G_1$, and then compare these values against predetermined threshold peak and width values to determine whether the acoustic coupling is sufficient. As an example, for some ultrasonic transducers the frequency may decrease from a frequency $f_1$ of about 44 kHz when uncoupled to a frequency $f_2$ of about 40 kHz when strongly coupled, causing a corresponding decrease in peak conductance from a first conductance value $G_1$ of about 0.01 Siemens to a second conductance value $G_2$ of about 0.0015 Siemens. In such case, a threshold for determining the coupling may comprise, for example, 0.003 Siemens. The particular frequency shift, conductance, and threshold values will typically vary, however, depending on the resonance characteristics of the acoustic transducer 16. For example, the frequency shift from $f_1$ to $f_2$ may vary from a relatively small shift for heavy acoustic transducers to a relatively large shift for lightweight, membrane type transducers.

In an alternative embodiment, the evaluation module 66 may use the measured complex impedance curves to extract equivalent electrical model parameters such as that described with respect to the equivalence electrical circuit 36 of FIG. 2. For example, for an acoustic transducer 16 with the equivalent model shown in FIG. 2, the value of the load resistance $R_M+R_L$ can be determined by the reciprocal of the conductance at the resonance peak. The coupling threshold criteria can then be set as the load resistance value that exceeds a predetermined load resistance value. By way of example and not limitation, for certain ultrasonic transducers the load resistance may shift from an initial load resistance value of about 50$\Omega$ when uncoupled to a second load resistance value at or above 400$\Omega$ when coupled. In such case, a threshold for determining the coupling may comprise, for example, a load resistance exceeding about 300$\Omega$. In a similar manner, the mechanical equivalent inductance $L_M$ could increase beyond a threshold value during adequate acoustic coupling, and can further serve as a coupling criteria, either alone or together with other extracted parameters and/or components.

In certain embodiments, the threshold coupling values comprise preprogrammed values contained within the controller 28 used to control the operation of the acoustic transducer 16. In other embodiments, the threshold coupling values may be fed to the controller 28 via the interface 30, from the patient management system 32, and/or from another device in communication with the controller 28. Since the maximum conductance value and the width of the conductance peak are indicators of the degree of acoustic coupling, these parameters can then be analyzed to determine whether sufficient coupling exists at the interface between the acoustic transducer 16 and the body.

Once the evaluation module 66 analyzes the maximum conductance and width parameters and compares these values against threshold peak and width values, the controller 28 may then output a signal to the patient via the interface 30 informing the patient of the current status of the acoustic coupling. The notification can occur visually (e.g., via a visual indicator or message on a computer monitor), audibly (e.g., via an audible sound indicating that the coupling is sufficient or insufficient), using a haptic indicator such as a vibration, or a combination of the above. In some embodiments, the controller 28 may also send a signal to the patient management system 32 informing a caregiver of the current status of the acoustic coupling. For example, the controller 28 may output a signal to the patient management system 32 in the event poor acoustic coupling is detected for a particular period of time (e.g., for a period of more than two hours). This information can then be used by a caregiver to determine whether corrective action may be required.

Figure 5:
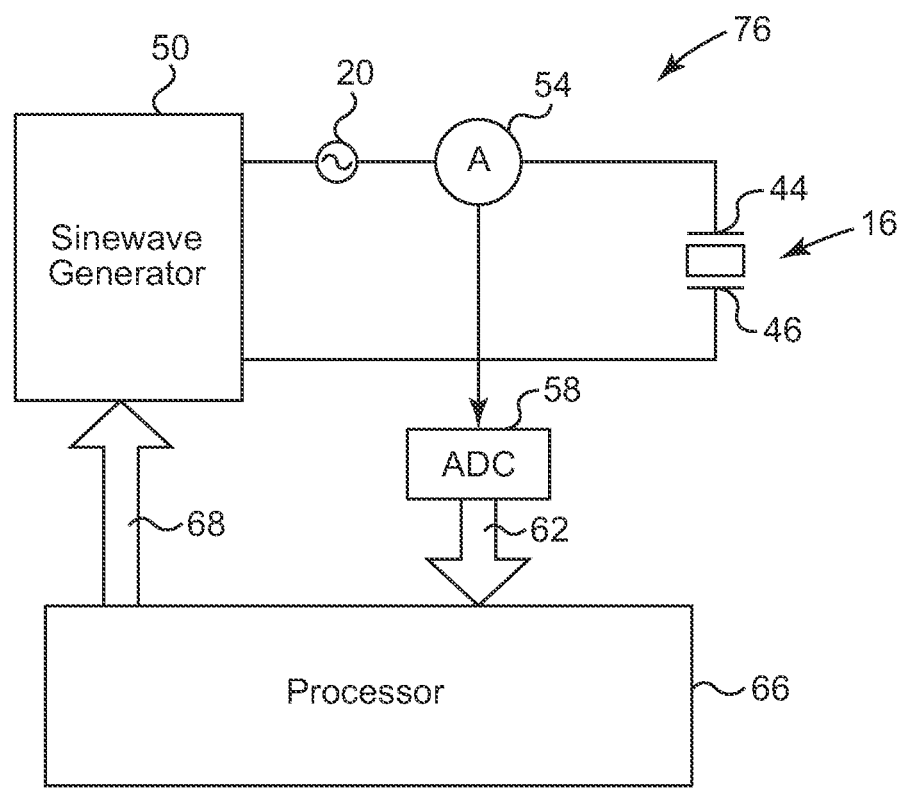
FIG. 5 is a block diagram showing another illustrative system for monitoring the acoustic coupling of an acoustic transducer attached to a patient's body.

FIG. 5 is a block diagram showing another illustrative system 76 for monitoring the acoustic coupling of an acoustic transducer 16 attached to a patient's body. The system 76 is similar to the system 48 of FIG. 3, but omits the voltmeter used for measuring the voltage differential across the transducer terminal leads 44,46. Instead, the evaluation module 66 is configured to substitute the measured voltage signal with an a priori known voltage signal (e.g. ±5V) from the signal generator 50. In certain embodiments, for example, the processor 66 may be pre-programmed with a known voltage output level from the signal generator 50. In other embodiments, the signal processor 50 may feed a signal to the evaluation module 66 that can be used to ascertain the voltage output level from the signal generator 50.

Figure 6:
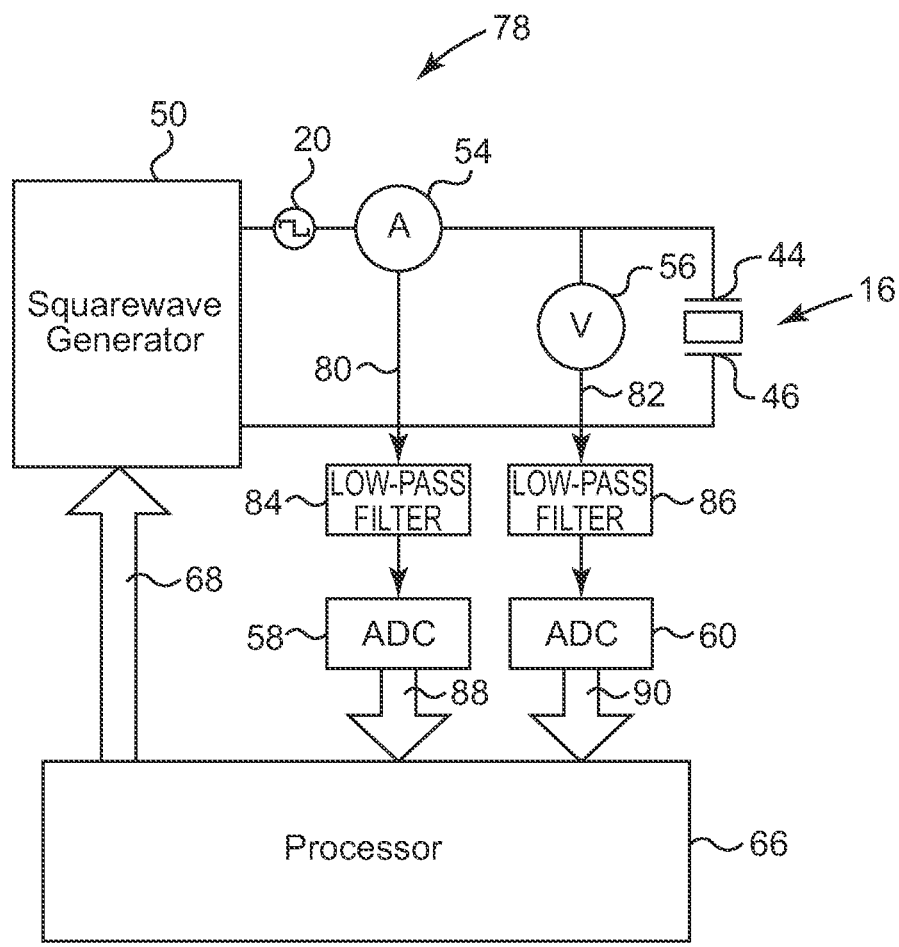
FIG. 6 is a block diagram showing another illustrative system for monitoring the acoustic coupling of an acoustic transducer attached to a patient's body.

FIG. 6 is a block diagram showing another illustrative system 78 for monitoring the acoustic coupling of an acoustic transducer 16 attached to a patient's body. In the illustrative embodiment of FIG. 6, the signal generator 50 supplies a square-wave electrical signal 20 to the acoustic transducer 16. The current and voltage signals 80,82 sensed by the ammeter 54 and voltmeter 56 are fed to respective low-pass filters 84,86 prior to being digitized, which eliminates the harmonics within the signals 80,82. The resulting signals 88,90 sent to the evaluation module 66 thus contain only the fundamental sine-wave constituents within the signals 80,82.

While filtering of the signals 80,82 can be performed using separate low-pass filters 84,86, in other embodiments the filtering can be performed by the current and voltage meters 54,56, or by the evaluation module 66. In one embodiment, for example, low-pass filtering of the digitized current and voltage signals 88,90 may be performed in software using the evaluation module 66.

In some embodiments, the impedance calculations are performed in hardware rather than in software. In certain embodiments, for example, the measured current and voltage signals 80,82 may be multiplied using an analog multiplier, and then averaged together using an integrator. Alternatively, and in other embodiments, the measured current and voltage signals 80,82 may be downshifted to baseband using an analog to digital mixer, which can be configured to separate each of the signals 80,82 into their phase and quadrature components before lowpass filtering. The resulting signals may be at a much lower frequency than the original current and voltage signals 80,82, and may thus be better suited for analysis by processors with lower computational and sampling capabilities.

Figure 7:
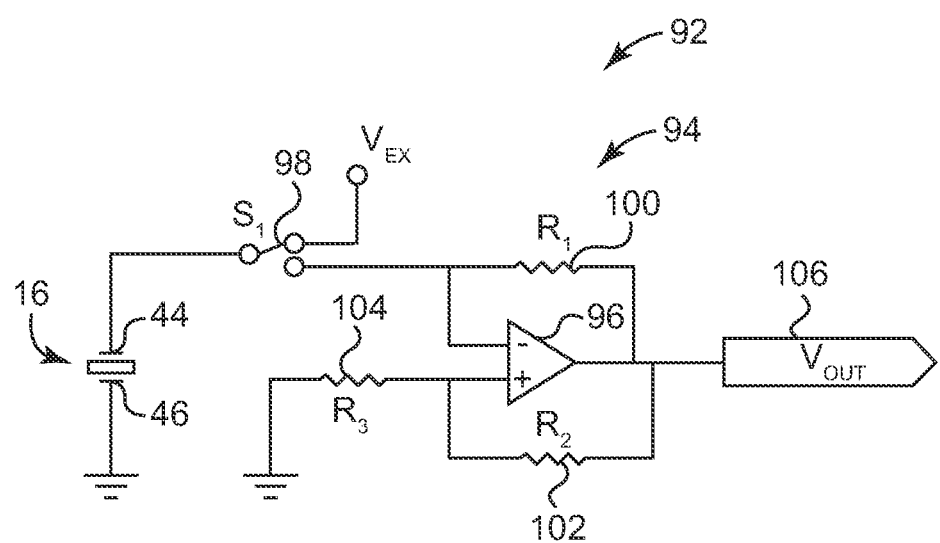
FIG. 7 is a circuit diagram showing another illustrative system for monitoring the acoustic coupling of an acoustic transducer attached to a patient's body.

FIG. 7 is a circuit diagram showing another illustrative system 92 for monitoring the acoustic coupling of an acoustic transducer attached to a patient's body. In the embodiment of FIG. 7, the system 92 includes a checking circuit 94 configured to evaluate the degree of acoustic coupling in the time domain rather than in the frequency domain. The circuit 94 includes an operational amplifier 96 selectively coupled to the acoustic transducer 16 through a switch 98 ($S_1$). The operational amplifier 96 includes a gain resistor 100 ($R_1$). In some embodiments, the operational amplifier 96 further includes a number of feedback resistors 102,104 ($R_2,R_3$) forming a positive feedback loop. The feedback loop can be used to compensate for the non-zero resistance of the switch 98. In those cases where the switch resistance is non-negligible, the resistors 102 and 104 can be selected such that the ratio of resistor 102 and resistor 104 (i.e., $R_3/R_2$) is equal to the ratio between the resistance of switch 98 and resistor 100 (i.e., $S_1/R_1$). This ensures that the zero volt condition is imposed directly on the terminal leads 44,46 of the acoustic transducer 16 rather than at the output of the switch 98, thus compensating for any additional dissipation that would otherwise be caused by the resistance of the switch 98.

In an initial state shown in FIG. 7, the switch 96 is initially toggled to apply an excitation voltage $V_{EX}$ to the acoustic transducer 16, thus charging the transducer 16 to that voltage $V_{EX}$. When the switch 96 is toggled to its second position at time t=0, the operational amplifier 96 forces the voltage on the acoustic transducer 16 to zero by means of the feedback resistors 102,104. This, in turn, imposes a step function voltage excitation on the acoustic transducer 16. The current through the acoustic transducer 16 then responds according to its time-domain admittance kernel Y(t) based on the following expression:

$$I(t) = V_{EX}\Theta(t) \otimes Y(t)$$
$$= V_{EX}\Theta(t) \otimes \sum_n A_n \exp(s_n t)$$
$$= \sum_n V_{EX} A_n \Theta(t) \otimes \exp(s_n t)$$

where $\Theta$ symbolizes the complimentary Heaviside step function, and $A_n$ and $s_n$ signify the pole position and amplitude of the admittance Laplace transform.

The convolution of a function with a step function returns the integral of the function evaluated at time t=0. Thus, the current is in the form of a sum of decaying exponentials as shown in the following expression:

$$I(t) = \sum_n V_{EX} A_n s_n^{-1} \exp(s_n t)$$

The above current flows through the resistor 100 ($R_1$), causing the output voltage $V_{OUT}$ of the circuit 94 to be:

$$V_{OUT} = R_1 I(t) = \sum_n V_{EX} A_n R_1 s_n^{-1} \exp(s_n t)$$

The output voltage 106 ($V_{OUT}$) is then subsequently fed to a processor and analyzed to determine the time-domain characteristics of the transducer response.

Figure 8A:
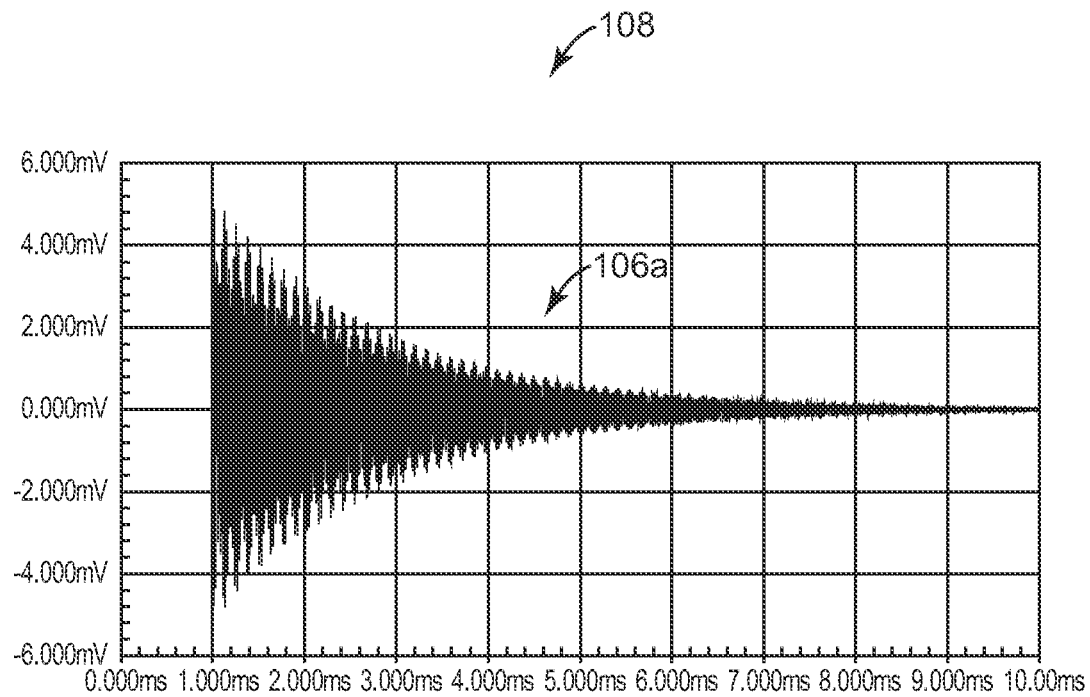
FIGS. 8A and 8B are graphs showing the output voltage versus time for the illustrative circuit of FIG. 7 for two different acoustic coupling scenarios.
Figure 8B:
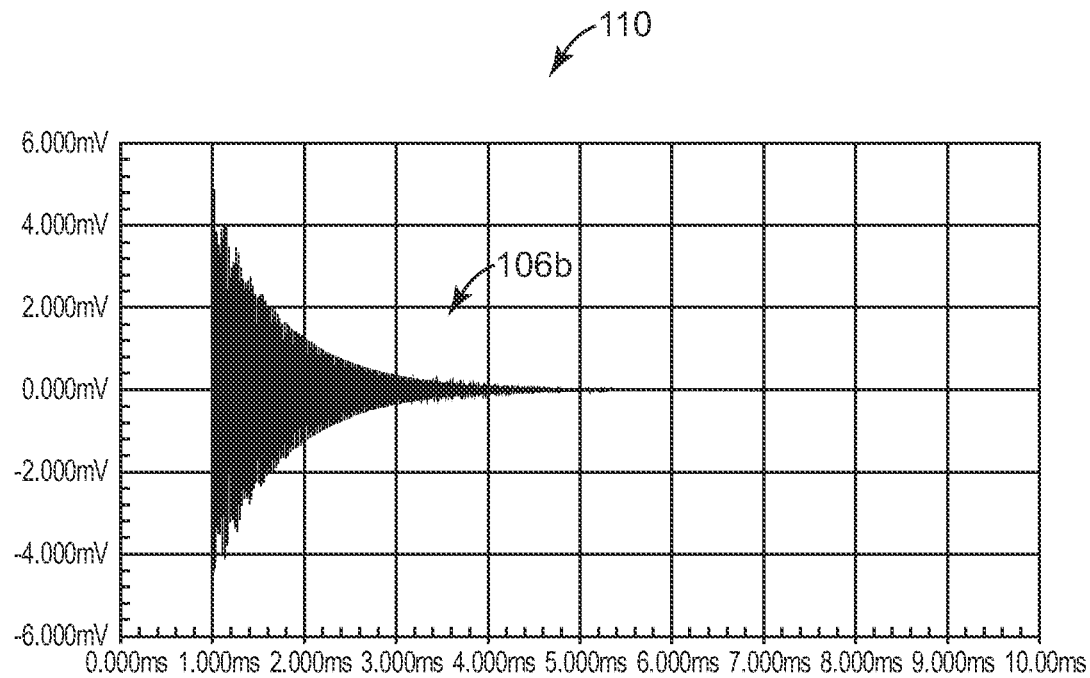

FIGS. 8A and 8B are graphs 108,110 showing the output voltage versus time for the illustrative circuit 94 of FIG. 7 during two different acoustic coupling scenarios. The first graph 108 in FIG. 8A may represent, for example, the output voltage 106a of the circuit 94 when the acoustic transducer 16 is operating in air whereas the second graph 110 in FIG. 8B may represent the output voltage 106b of the circuit 94 when the transducer 16 is operating in water. As can be seen by a comparison of the two graphs 108,110, the output voltage 106a when the acoustic transducer 16 is operating in air decays at a slower rate than the output voltage 106b during in-water operation. In addition, for in-air operation, the output voltage 106a exhibits two different frequencies, which can be observed in FIG. 8A as the beat observed in the amplitude. In comparison, and as shown in FIG. 8B, the acoustic transducer exhibits a less pronounced beat frequency during in-water operation than during in-air operation.

In use, the circuit 94 can be used to evaluate the degree of acoustic coupling between the acoustic transducer 16 and the patient's body by measuring the decay time of the output voltage 106. In some embodiments, for example, the degree of acoustic coupling can be determined by estimating the amplitude envelope of the output voltage 106, and then calculating a decay rate associated with the envelope. An example decay rate for an ultrasonic transducer sufficiently coupled to the body, for instance, may be less than about 1 ms, although other decay rates are possible depending on the type of transducer employed. In some embodiments, the amplitude envelope detection can be performed by analog circuitry such as an RMS detector or a diode followed by a low-pass filter. Alternatively, and in other embodiments, the output voltage 106 can be sampled directly into a processor, and the decay rate calculation performed in software.

In certain embodiments, the output voltage 106 may be sampled into a processor adapted to run an algorithm that directly evaluates the frequency and decay of each constituent decaying exponent separately. In such case, the output voltage 106 may comprise the sum of several exponentials, where only the decay rate of some of the exponentials depends on the acoustic coupling. This may occur, for example, when the acoustic transducer 16 also includes a matching circuit that imposes a strong electrical resonance that is insensitive to the acoustic coupling, but which is sensitive to the underlying mechanical resonance of the circuit. In this situation, an analysis of the decay time for the relevant exponential or exponentials that exhibit sensitivity to the acoustic coupling rather than determining the decay time of an amplitude envelope may be utilized.

An example algorithm that can be used to decompose a signal into a sum of decaying exponentials is the Prony algorithm, which uses raw data to generate a polynomial whose roots are related to the frequency and decay rate of the exponentials. An algorithm can be used to root the polynomial to find the position of the amplitude using any variety of known rooting methods. The degree of acoustic coupling can then be determined by examining those roots that are affected by the coupling. Typically, the presence of the acoustic coupling will cause the real portion of these roots, which signifies their decay rate, to increase. The presence of sufficient acoustic coupling can then be determined when the real portion of the roots crosses a predetermined threshold. In some cases, the imaginary part of the root position will change as well due to the additional mass that results when the acoustic transducer is sufficiently coupled to the patient's body, which causes the mechanical resonance frequency to decrease. Thus, in some embodiments, the change in imaginary root position is also used as an indication of the degree of acoustic coupling that is present.

In another embodiment, the output voltage 106 from the circuit 94 may be sampled into a processor adapted to run an algorithm that evaluates the degree of acoustic coupling without requiring an explicit rooting of the polynomial in a complex plane. An example means to accomplish this utilizes the Caucy Argument Principle, which states that for a given meromorphic function $f(z)$ in the complex plane:

$$\frac{1}{2\pi}\text{Im}\oint_C \frac{f'(z)}{f(z)}dz = N_{zeros} - N_{poles}$$

In the above expression, C is the contour surrounding the region of interest in the complex plane, and $N_{zeros}$ and $N_{poles}$ are the number of zeros and poles, respectively, enclosed by the contour C. The f'(z) term in the above expression denotes the derivative with respect to z, "f(z)" is set to be the Prony polynomial, and the contour C is the contour enclosing the region in the complex space where a coupling-sensitive zero is expected to be when the transducer is operating in air. By performing the contour integration using these parameters, a result of approximately 1 would be returned if a zero lies within the contour region, thus indicating that the acoustic transducer 16 is not adequately coupled. Conversely, the relevant zero will wander to a different location and the integral will return a result of approximately zero when the acoustic transducer 16 is sufficiently coupled. Based on the result from this integration, a determination of the degree of acoustic coupling can thus be made.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system for monitoring the acoustic coupling of an acoustic transducer attached to a patient's body, comprising:
   an acoustic transducer attachable to the body and in acoustic communication with an implantable medical device;
   a signal generator coupled to the acoustic transducer, the signal generator adapted to supply a time-varying electrical signal to the acoustic transducer for generating an acoustic wave;
   a circuit configured to measure at least one electrical parameter of the acoustic transducer in response to the electrical signal while the transducer is acoustically loaded to a tissue interface of the body, the at least one electrical parameter including a frequency parameter associated with a frequency-dependent response of the acoustic transducer to the time-varying electrical signal; and
   an evaluation module adapted to evaluate the degree of acoustic coupling of the loaded transducer to the tissue interface by evaluating a complex impedance curve associated with the loaded transducer based at least in part on the measured frequency parameter, wherein the evaluation module is configured to evaluate the degree of acoustic coupling by causing the signal generator to sweep the electrical signal across a frequency range and measure a corresponding impedance parameter at each of a plurality of frequencies in the frequency range, wherein the evaluation module is further configured to analyze a width of the complex impedance curve.

2. The system of claim 1, wherein the at least one electrical parameter further includes a measured voltage or current parameter.

3. The system of claim 1, wherein the circuit comprises a time domain coupling circuit.

4. The system of claim 3, wherein the evaluation module is further configured to evaluate the acoustic coupling based on a time domain parameter associated with the acoustic transducer.

5. The system of claim 3, wherein the evaluation module is configured to evaluate the acoustic coupling based on a time-domain parameter and the frequency parameter associated within the acoustic transducer.

6. A method of monitoring the acoustic coupling of an acoustic transducer attached to a patient's body, comprising:
   providing a time-varying electrical signal to the acoustic transducer;
   measuring at least one electrical parameter associated with the response of the acoustic transducer to the electrical signal while the transducer is acoustically loaded to a tissue interface of the body, the at least one electrical parameter including a frequency parameter associated with a frequency-dependent response of the acoustic transducer to the time-varying electrical signal; and
   evaluating the degree of acoustic coupling of the loaded acoustic transducer to the tissue interface by evaluating a complex impedance curve associated with the loaded transducer based at least in part on the measured frequency parameter, wherein evaluating the degree of acoustic coupling comprises sweeping the electrical signal across a frequency range and measuring a corresponding impedance parameter at each of a plurality of frequencies in the frequency range, and wherein evaluating the degree of acoustic coupling further comprises analyzing a width of the complex impedance curve.

7. The method of claim 6, wherein the at least one electrical parameter further includes a voltage parameter associated with the acoustic transducer.

8. The method of claim 6, wherein the at least one electrical parameter further includes a current parameter associated with the acoustic transducer.

9. The method of claim 6, further comprising outputting a warning signal if the degree of acoustic coupling falls below a threshold coupling value.

10. The method of claim 6, wherein evaluating the degree of acoustic coupling of the acoustic transducer to the body further includes measuring a time domain parameter associated with the response of the acoustic transducer to the electrical signal.

11. The method of claim 6, wherein evaluating the degree of acoustic coupling of the acoustic transducer to the body includes measuring both the frequency parameter and a time domain parameter associated with the response of the acoustic transducer to the electrical signal.

12. The method of claim 6, wherein evaluating the degree of acoustic coupling of the acoustic transducer to the body further includes measuring the load resistance or mechanical inductance of an equivalence electrical circuit modeling the acoustic transducer.

13. A method of monitoring the acoustic coupling of an acoustic transducer attached to a patient's body, comprising:
   providing a time-varying electrical signal to an acoustic transducer acoustically loaded to a tissue interface of the body, the transducer including a number of terminal leads;
   measuring a voltage parameter at the terminal leads in response to the electrical signal;
   measuring a current parameter across the terminal leads in response to the electrical signal;
   measuring a frequency parameter associated with a frequency-dependent response of the loaded acoustic transducer to the electrical signal; and evaluating the degree of acoustic coupling of the acoustic transducer to the tissue interface by evaluating a complex impedance curve associated with the loaded transducer based at least in part on the measured voltage, current, and frequency parameters, wherein evaluating the degree of acoustic coupling comprises sweeping the electrical signal across a frequency range and measuring a corresponding impedance parameter at each of a plurality of frequencies in the frequency range, and wherein evaluating the degree of acoustic coupling further comprises analyzing a width of the complex impedance curve.

* * * * *